(12) United States Patent
Hesselroth et al.

(10) Patent No.: US 7,022,658 B2
(45) Date of Patent: Apr. 4, 2006

(54) AZEOTROPE-LIKE COMPOSITIONS CONTAINING HEXAFLUOROPROPYLENE DIMER AND USE THEREOF

(75) Inventors: David A. Hesselroth, Hudson, WI (US); John G. Owens, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 235 days.

(21) Appl. No.: 10/673,821

(22) Filed: Sep. 29, 2003

(65) Prior Publication Data

US 2005/0070455 A1 Mar. 31, 2005

(51) Int. Cl.
*B01D 3/36* (2006.01)

(52) U.S. Cl. .................. 510/409; 510/408; 510/412

(58) Field of Classification Search .................. None
See application file for complete search history.

(56) References Cited

U.S. PATENT DOCUMENTS

| | | | |
|---|---|---|---|
| 4,972,002 A | | 11/1990 | Volkert |
| 5,026,499 A | * | 6/1991 | Merchant ................ 252/67 |
| 5,254,774 A | | 10/1993 | Prokop |
| 5,631,306 A | | 5/1997 | Dams et al. |
| 6,030,934 A | | 2/2000 | Owens et al. |
| 6,242,410 B1 | * | 6/2001 | Aoyama et al. ........... 510/409 |
| 6,423,673 B1 | | 7/2002 | Owens et al. |
| 6,630,075 B1 | * | 10/2003 | Behr et al. ............ 252/183.11 |

FOREIGN PATENT DOCUMENTS

| | | |
|---|---|---|
| DE | 2706297 A1 | 8/1978 |
| FR | 2 829 773 | 3/2003 |

OTHER PUBLICATIONS

D. Rosbotham et al., "HFC-134a-A Zero O.D.P. Option for Rigid Polyurethane Foam," *Proceedings of the SPI 34th Annual Polyurethane Technical/Marketing Conference*, New Orleans, LA, Oct. 21-24, 1992.

"Amendment to the Montreal Protocol on Substances That Deplete The Ozone Layer," Copenhagen Amendments, United Nations Environment Program, 1992.

R. Atkinson et al., "Kinetics And Mechanisms Of The Reactions Of The Hydroxyl Radical With Organic Compounds In The Gas Phase", *Advances in Photochemistry*, An Interscience Publication, John Wiley & Sons, vol. 11, 1979, pp. 375-488.

J. H. Saunders and K. C. Frisch, High Polymers, vol. XVI, "Polyurethanes, Chemistry and Technology" Part I, vol. XVI, pp. 32-54 and 65-88, *Interscience*, New York, 1962.

(Continued)

*Primary Examiner*—Gregory E. Webb
(74) *Attorney, Agent, or Firm*—Kent S. Kokko

(57) ABSTRACT

Azeotrope-like compositions comprising hexafluoropropylene dimer and a hydrocarbon or a hydrofluorocarbon, and uses thereof, are described.

4 Claims, 4 Drawing Sheets

OTHER PUBLICATIONS

B. N. Ellis, "Cleaning and Contamination Of Electronics Components And Assemblies", *Electrochemical Publications Limited*, Ayr, Scotland, pp. 182-194, 1986.

Hawley's Condensed Chemical Dictionary, 13th Edition, Van Nostrand Reinhold Company, 1993.

"The Use of Azeotrope and Azeotrope-Like Blowing Agent Mixtures in Polyurethane Foam", Research Disclosure, Kenneth Mason Publications, Hampshire, GB, vol. 309, No. 50, Oct. 1996.

\* cited by examiner

AZEOTROPE-LIKE COMPOSITIONS CONTAINING HEXAFLUOROPROPYLENE DIMER AND USE THEREOF

FIELD OF THE INVENTION

This invention relates to azeotrope-like compositions containing hexafluoropropylene dimer. In other aspects, this invention relates to methods of using azeotropes and azeotrope-like compositions to clean substrates, deposit coatings, transfer thermal energy, lubricate working operations, and aid in foam blowing.

BACKGROUND OF THE INVENTION

Chlorofluorocarbons (hereinafter, CFCs) have been widely used as blowing agents for producing polymeric foams. However, the photolytic and homolytic reactivity at the chlorine-containing carbon sites has been shown to contribute to depletion of the earth's ozone layer. Additionally, the long atmospheric lifetime of CFCs has been linked to global warming. As a result, there has been a world-wide movement for over a decade to replace CFCs. (See "Montreal Protocol on Substances That Deplete the Ozone Layer," Copenhagen Amendments, United nations Environment Program, 1992;

The characteristics sought in replacements to CFCs include boiling point ranges suitable for a variety of applications, low flammability, and low toxicity. One approach to developing CFC replacements has been to substitute hydrogen atoms for chlorine atoms so as to provide hydrochlorofluorocarbons (hereinafter, HCFCs) or hydrofluorocarbons (hereinafter, HFCs). HCFCs and HFCs have lower ozone depletion potentials (HFCs have zero ozone depletion potential) and shorter atmospheric lifetimes than CFCs. Unfortunately, HCFCs and HFCs are inferior to CFCs as foam blowing agents. (D. Rosbotham et al. in "HFC-134a—A Zero O.D.P. Option for Rigid Polyurethane Foam," Proceedings of the SPI 34th Annual Polyurethane Technical/Marketing Conference, New Orleans, La. Oct. 21–24, 1992). The phase out of HCFC-141b has prompted many manufacturers of closed-cell, polyurethane foam to use alternative blowing agents.

Azeotropes and azeotrope-like con positions possess properties that make them useful foam blowing agents and solvents. For example, azeotropes and azeotrope-like compositions have a constant boiling point that avoids boiling temperature drift during processing and use. In addition, when an azeotrope or azeotrope-like composition is used as a foam-blowing agent, the properties of the foam can remain constant because the composition of the foam-blowing agent does not change during use. Azeotropes that are used as solvents also can be recovered conveniently by distillation.

Thus, there is a need for azeotropes or azeotrope-like compositions that are effective foam-blowing agents, and may also have good solvent strength, low flammability, are non-ozone depleting, and have a relatively short atmospheric lifetime so that they have a low global warming potential.

SUMMARY

Briefly, the present invention provides azeotropes and azeotrope-like compositions. The compositions comprise (a) hexafluoropropylene dimer and (b) a second hydrocarbon or a hydrofluorocarbon component selected from cyclopentane, n-pentane, isopentane and 1,1,1,3,3-pentafluorobutane.

While the concentrations of hexafluoropropylene dimer and hydrofluorocarbon or hydrocarbon may vary somewhat from the concentrations found in the azeotrope formed between them, the boiling points of the azeotrope-like compositions are below the boiling point of the minimum boiling point component. Thus, the azeotrope-like compositions of the present invention include the corresponding azeotrope.

The foamable compositions of the invention comprising hexafluoropropylene dimer and hydrofluorocarbon or hydrocarbon as co-blowing agents generally provide polymeric foams having a smaller cell size (and therefore better insulation efficiency) than foams produced using only conventional blowing agents such as CFCs, HCFCs, HFCs, hydrocarbons, hydrochlorocarbons, or water. The compositions of the invention also have a lower ozone depletion potential (zero) than some conventional blowing agents, e.g. CFCs and HCFCs. Also, the compositions of this invention have shorter atmospheric lifetimes (due to their greater reactivity) than HFCs or saturated perfluorochemical blowing agents (or blowing agent additives), and thus present a lower overall global warming potential. (See, e.g., R. Atkinson et al., Adv. Photochem. 11, 375 (1979)).

In another aspect, this invention provides a process for preparing polymeric foams. This process may involve vaporizing an azeotrope-like composition comprising hexafluoropropylene dimer and a hydrocarbon or a hydrofluorocarbon as provided in the presence of at least one foamable polymer or the precursors of at least one foamable polymer. As used herein, reactive components that react with one another either during or after foaming to form a foamable polymer are regarded as precursors of a foamable polymer.

In other aspects, this invention provides polymeric foams prepared from this process, and articles comprising the foams. The foams can vary from very soft types useful in upholstery applications to rigid foams useful as structural or insulating materials. It is also contemplated that the azeotrope-like compositions of this invention may be used in cleaning processes, coating compositions and processes, fully volatile working fluids, and as heat transfer agents.

In another aspect, the present invention provides a method of cleaning objects by contacting the object to be cleaned with one or more of the azeotrope-like compositions of this invention or the vapor of these compositions until undesirable contaminants or soils on the object are dissolved, dispersed, or displaced, and rinsed away.

The present invention also provides coating compositions comprising an azeotrope-like composition and coating material that are useful in the coating process.

In yet another aspect, the present invention provides a method of depositing coating compositions on substrates using the azeotrope-like compositions as solvents or carriers for the coating material. The process comprises the step of applying to at least a portion of at least one surface of a substrate a coating composition comprising: (a) an azeotrope-like composition; and (b) at least one coating material that is soluble or dispersible in the azeotrope-like composition. Preferably, the process further comprises the step of removing the azeotrope-like composition from the coating composition, for example, by evaporation.

The azeotrope-like compositions of the present invention are also useful in fully volatile working fluids. These working fluids act to lubricate the cutting or forming processes used to fabricate metal, cermet, and composite parts and fully evaporate from the surfaces leaving little, if any, residue.

In yet another aspect, the present invention provides a method of transferring thermal energy using the azeotrope-like compositions as heat-transfer fluids.

DETAILED DESCRIPTION OF THE INVENTION

An azeotropic composition or azeotrope is a constant boiling liquid mixture of two or more substances that behaves like a single substance in that the vapor produced by partial evaporation of liquid at its boiling point has the same composition as the liquid. Azeotropic compositions are constant boiling mixtures that exhibit either a maximum or minimum boiling point as compared with other compositions of the same substances.

Figure 1:
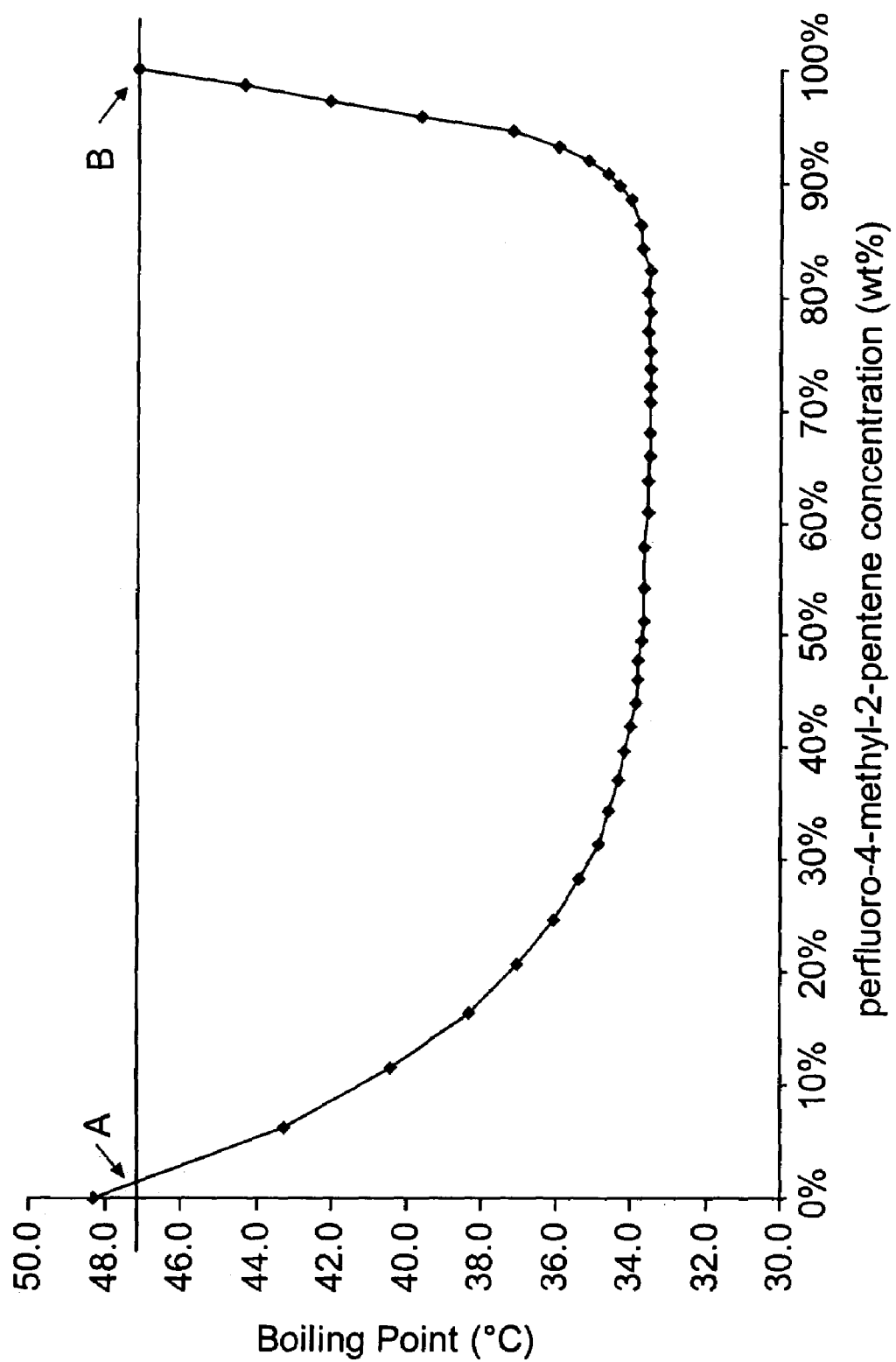
FIGS. 1 to 4 are the vapor pressure curves for Examples 1 to 4, respectively
Figure 2:
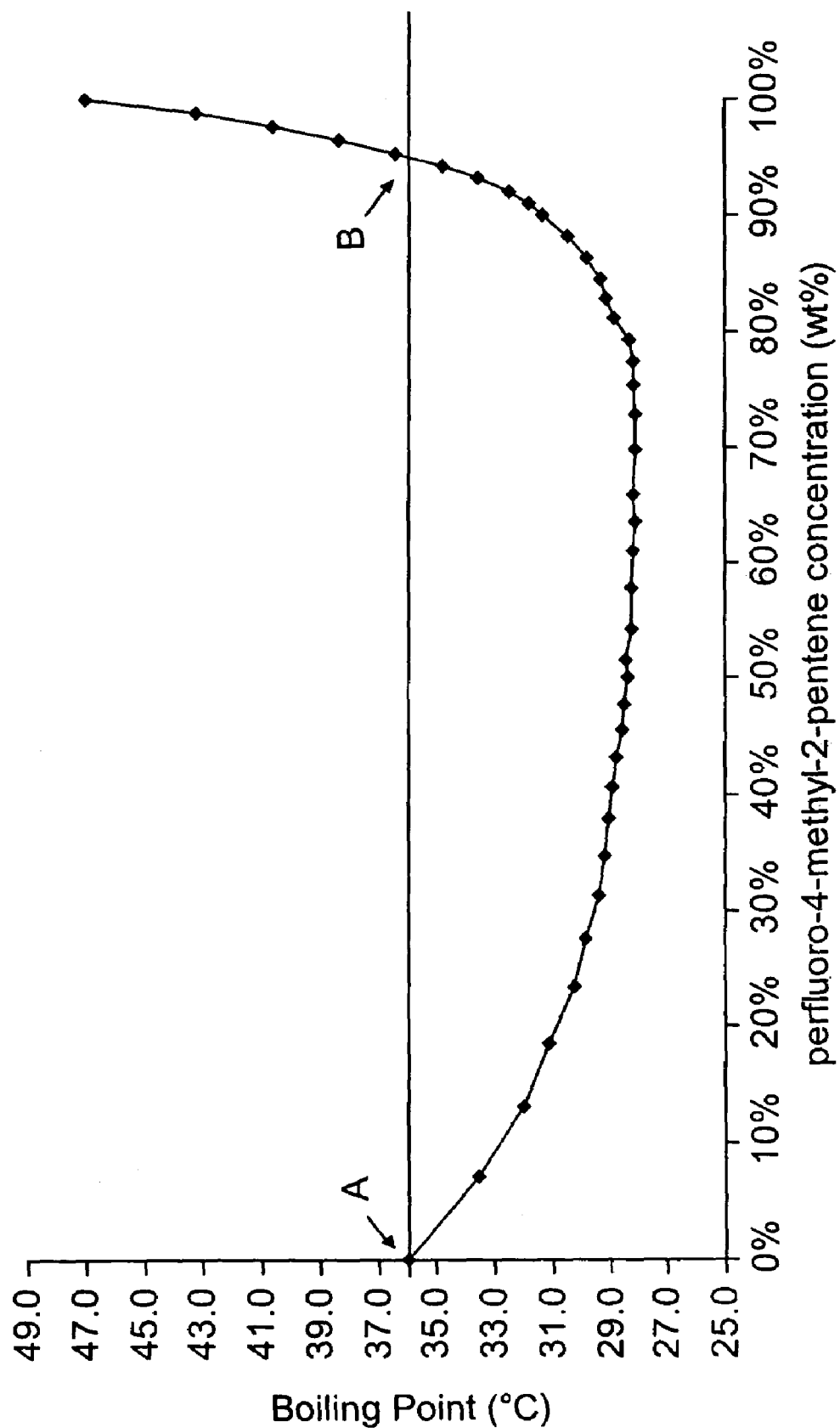
Figure 3:
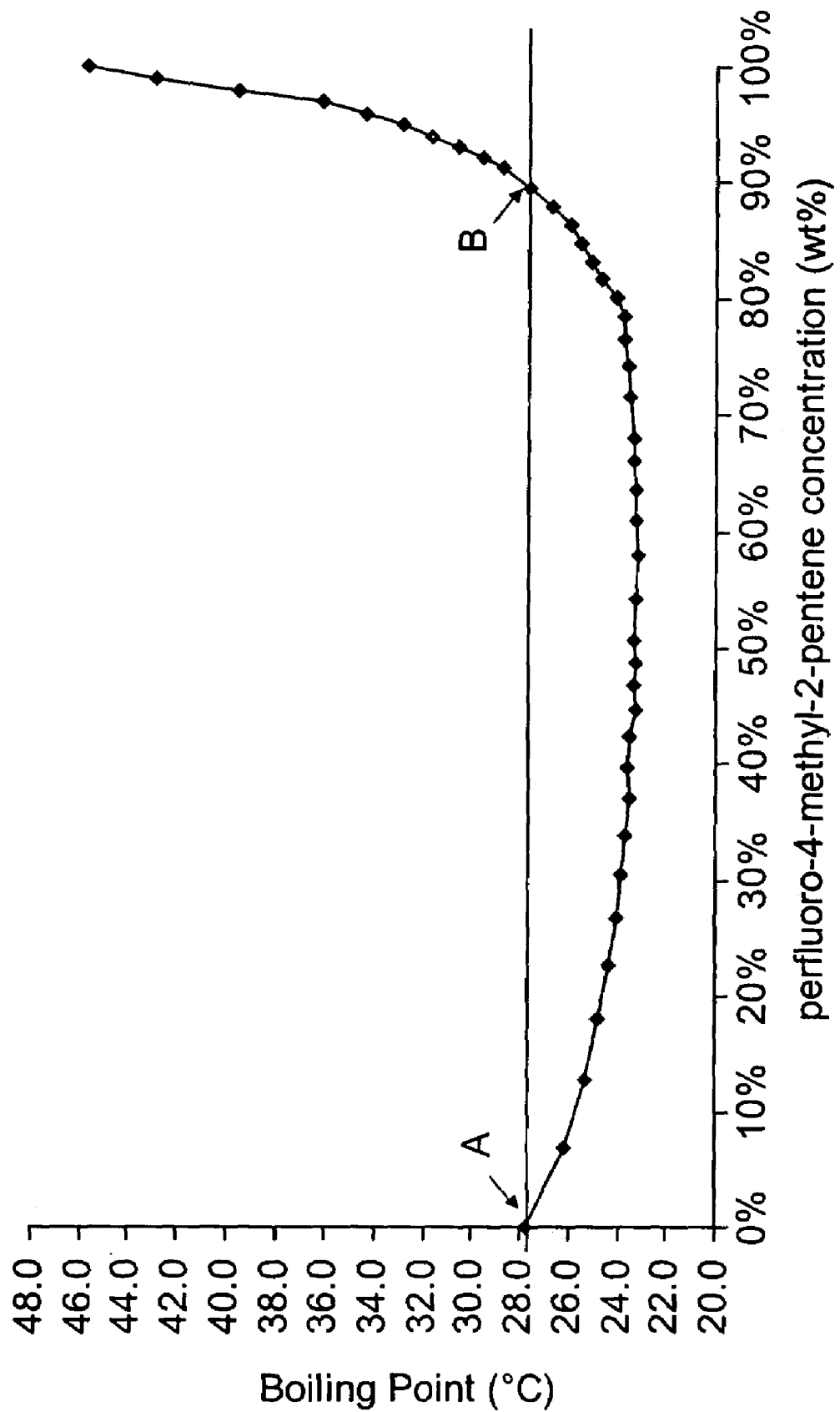
Figure 4:
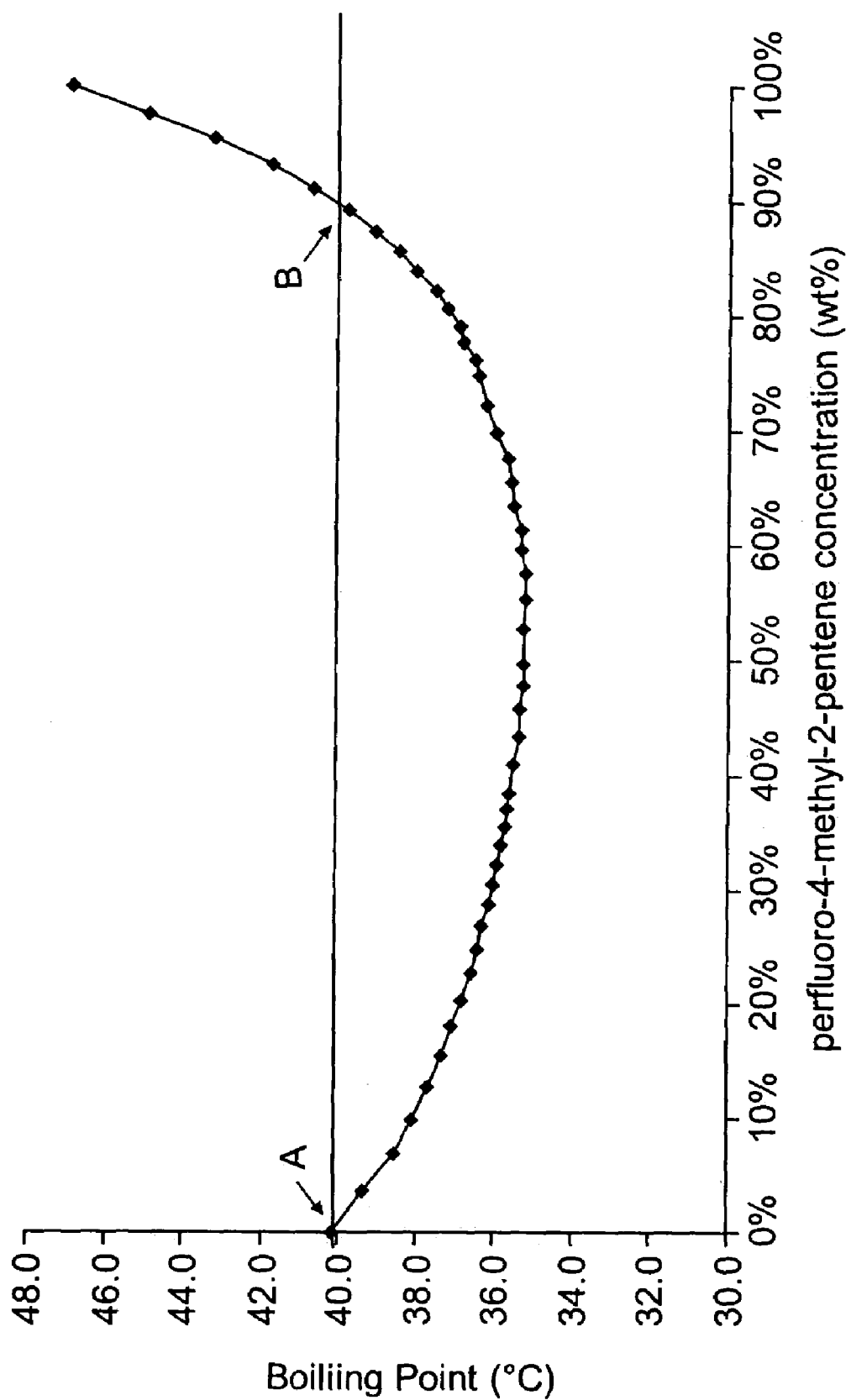

An azeotrope-like composition includes the corresponding azeotrope. Azeotrope-like compositions of the present invention are mixtures of hexafluoropropylene dimer and a hydrocarbon or a hydrofluorocarbon that exhibit strong thermodynamic non-ideality. A thermodynamically ideal or slightly non-ideal mixture has a boiling point between the boiling points of the two components. But the azeotrope-like compositions of the present invention boil at temperatures that are below the boiling point of the minimum boiling point component. See FIGS. 1 to 4.

The concentration of hexafluoropropylene dimer and hydrocarbon or hydrofluorocarbon in a particular azeotrope-like composition may vary substantially from the corresponding azeotropic composition, and the magnitude of this permissible variation depends upon the hydrocarbon or hydrofluorocarbon. More preferably, the azeotropic-like composition contains essentially the same concentrations of hexafluoropropylene dimer and hydrocarbon or hydrofluorocarbon as are contained in the azeotrope formed between them at ambient pressure. The preferred compositions exhibit no significant change in the solvent power of the composition over time.

Azeotropes retain many of the properties of the individual component solvents, which can enhance performance and usefulness over the individual components because of the combined properties. Azeotrope-like compositions of this invention may also contain, in addition to the hexafluoropropylene dimer and hydrocarbon or hydrofluorocarbon, small amounts of compounds that do not interfere in the formation of the azeotrope. For example, co-solvents may be added to improve the thermal insulating properties of the polymeric foam of the present invention.

Hexafluoropropylene dimer is the first component of the azeotrope-like composition of the current invention. The relative amount of hexafluoropropylene dimer to hydrocarbon or hydrofluorocarbon can vary depending upon the identity of the second component. Since hexafluoropropylene dimer is both the more expensive and the value-added component of the current invention (i.e., it provides for the increase in thermal insulation provided by the polymeric foam of the present invention), it is contemplated that one skilled in the art would adjust the relative ratio of the two components so as to achieve the ideal balance of cost and performance for the application at hand.

Hexafluoropropylene (HFP), in the presence of fluoride ion, forms a heptafluoropropylene anion of the formula $(CF_3—)_2CF$ that may react with hexafluoropropylene itself to form product dimers, as well as byproduct trimers and higher molecular weight oligomers. In general, the kinetic dimer isomers of HFP form quickly in the presence of fluoride ion, and are converted to the thermodynamic dimer over time. The dimer byproducts have two kinetic isomers and a thermodynamic isomer. With respect to the azeotrope-like and azeotropic compositions, any of the following isomers, or mixtures thereof may be used to prepare the compositions of the present invention, although the kinetic isomers, and mixtures thereof are preferred. Due to toxicity considerations it is preferred that the azeotropes and azeotrope-like compositions contain less than 5 wt %, preferably less than 1 wt. %, most preferably less than 0.1 wt. % of the thermodynamic isomer.

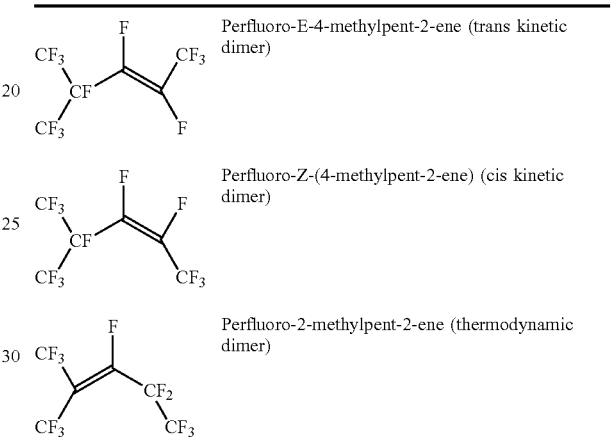

The second component of the azeotropes is selected from a hydrocarbon or hydrofluorocarbon compound. The hydrocarbons include cyclopentane, n-pentane, and isopentane. The hydrofluorocarbon of this invention is 1,1,1,3,3-pentafluorobutane. As noted above, the relative amount of hydrocarbon or hydrofluorocarbon in the present azeotrope-like compositions can vary.

Azeotrope-like compositions comprising hexafluoropropylene dimer and a hydrocarbon or a hydrofluorocarbon include the following:

(a) hexafluoropropylene dimer; and (b) a hydrocarbon or a hydrofluorocarbon;

wherein said composition is selected from the group consisting of:

(i) compositions consisting essentially of about 2 to about 99 weight percent hexafluoropropylene dimer and about 1 to about 98 weight percent cyclopentane that boil below about 47° C. at about 760 torr;

(ii) compositions consisting essentially of about 1 to about 95 weight percent hexafluoropropylene dimer and about 5 to about 99 weight percent n-pentane that boil below about 36° C. at about 760 torr;

(iii) compositions consisting essentially of about 1 to about 90 weight percent hexafluoropropylene dimer and about 10 to about 99 weight percent isopentane that boil below about 27.5° C. at about 760 torr; and (iv) compositions consisting essentially of about 1 to about 90 weight percent hexafluoropropylene dimer and about 10 to about 99 weight percent 1,1,1,3,3-pentafluorobutane that boil below about 40° C. at about 760 torr.

Preferably these azeotrope-like compositions have a boiling point less than 75% of boiling point depression from the lowest boiling component to the minimum boiling point of the azeotrope-like composition. These preferred azeotrope-like compositions comprising hexafluoropropylene dimer and a hydrocarbon or a hydrofluorocarbon include the following:
  (a) hexafluoropropylene dimer; and
  (b) a hydrocarbon or a hydrofluorocarbon;
    wherein said composition is selected from the group consisting of:
    (i) compositions consisting essentially of about 5 to about 98 weight percent hexafluoropropylene dimer and about 2 to about 95 weight percent cyclopentane that boil below about 44° C. at about 760 torr;
    (ii) compositions consisting essentially of about 5 to about 94 weight percent hexafluoropropylene dimer and about 6 to about 95 weight percent n-pentane that boil below about 34° C. at about 760 torr;
    (iii) compositions consisting essentially of about 5 to about 88 weight percent hexafluoropropylene dimer and about 12 to about 95 weight percent isopentane that boil below about 27° C. at about 760 torr; and
    (iv) compositions consisting essentially of about 5 to about 87 weight percent hexafluoropropylene dimer and about 13 to about 95 weight percent 1,1,1,3,3-pentafluorobutane that boil below about 39° C. at about 760 torr.

More preferably these azeotrope-like compositions have a boiling point less than 50% of boiling point depression from the lowest boiling component to the minimum boiling point of the azeotrope-like composition. Such preferred azeotrope-like composition includes the following:
  (a) hexafluoropropylene dimer; and
  (b) a hydrocarbon or a hydrofluorocarbon;
    wherein said composition is selected from the group consisting of:
    (i) compositions consisting essentially of about 12 to about 96 weight percent hexafluoropropylene dimer and about 4 to about 88 weight percent cyclopentane that boil below about 40° C. at about 760 torr;
    (ii) compositions consisting essentially of about 13 to about 91 weight percent hexafluoropropylene dimer and about 9 to about 87 weight percent n-pentane that boil below about 32° C. at about 760 torr;
    (iii) compositions consisting essentially of about 11 to about 85 weight percent hexafluoropropylene dimer and about 15 to about 89 weight percent isopentane that boil below about 26° C. at about 760 torr; and
    (iv) compositions consisting essentially of about 10 to about 84 weight percent hexafluoropropylene dimer and about 16 to about 90 weight percent 1,1,1,3,3-pentafluorobutane that boil below about 38° C. at about 760 torr.

The azeotrope compositions containing hexafluoropropylene dimer and a hydrocarbon or a hydrofluorocarbon include the following:
  (a) hexafluoropropylene dimer; and
  (b) a hydrocarbon or a hydrofluorocarbon;
    wherein said composition is selected from the group consisting of:
    (i) compositions consisting essentially of about 77.4 weight percent hexafluoropropylene dimer and about 22.6 weight percent cyclopentane that boil at about 32° C. at about 729 torr;
    (ii) compositions consisting essentially of about 67.5 weight percent hexafluoropropylene dimer and about 32.5 weight percent n-pentane that boil at about 27° C. at about 731 torr;
    (iii) compositions consisting essentially of about 58.6 weight percent hexafluoropropylene dimer and about 41.4 weight percent isopentane that boil at about 22° C. at about 735 torr; and
    (iv) compositions consisting essentially of about 54.4 weight percent hexafluoropropylene dimer and about 45.6 weight percent 1,1,1,3,3-pentafluorobutane that boil at about 34° C. at about 730 torr.

Preferably, the azeotrope-like compositions are homogenous, i.e., they form a single phase, under ambient conditions, i.e., at room temperature and at atmospheric pressure.

Polymeric foams can be prepared using foamable compositions (i.e., azeotrope-like compositions and at least one foamable polymer or the precursors of at least one foamable polymer) by vaporizing (e.g., by utilizing the heat of precursor reaction) at least one azeotrope-like composition in the presence of at least one foamable polymer or the precursors of at least one foamable polymer.

In one embodiment precursors of the foamable polymer of the present invention include a polyol and an isocyanate. In making the polyisocyanate-based foam, the isocyanate (or polyisocyanate), polyol and azeotrope-like composition can generally be combined, thoroughly mixed (using, e.g., any of the various known types of mixing head and spray apparatus), and permitted to expand and cure into a cellular polymer.

It is often convenient, but not necessary to preblend certain of the components of the foamable composition prior to reaction of the isocyanate and the polyol. For example, the azeotrope-like composition may be added to the polyol to form a first mixture and then blended with the isocyanate before vaporization and polymeric foam formation. Alternatively, the azeotrope-like composition can be added to the isocyanate to form a first mixture and then blended with the polyol before vaporization and polymeric foam formation. One can add hexafluoropropylene dimer to the isocyanate to form a pre-mixture, then add the hydrocarbon or hydrofluorocarbon and then bend the resultant mixture with the polyol. As well, one can add hexafluoropropylene dimer to the polyol to form a pre-mixture and then add the hydrocarbon or hydrofluorocarbon and then bend the resultant mixture with the isocyanate. In another aspect, hexafluoropropylene dimer is added to the polyol to form a first pre-mixture, the hydrocarbon or hydrofluorocarbon is added to the isocyanate to form a second pre-mixture and the first and second pre-mixtures are blended together. Also, hexafluoropropylene dimer can be added to the isocyanate to form a first pre-mixture, the hydrocarbon or hydrofluorocarbon is added to the polyol to form a second pre-mixture and the first and second pre-mixtures are blended together.

Polyisocyanates (or isocyanate precursors) suitable for use in the process of this invention include aliphatic, alicyclic, arylaliphatic, aromatic, or heterocyclic polyisocyanates, or combinations thereof. Any polyisocyanate that is suitable for use in the production of polymeric foams can be utilized. Of particular importance are aromatic diisocyanates such as toluene and diphenylmethane diisocyanates in pure, modified, or crude form. MDI variants (diphenylmethane diisocyanate modified by the introduction of urethane, allophanate, urea, biuret, carbodiimide, uretonimine, or isocyanurate residues) and the mixtures of diphenylmethane diisocyanates and oligomers thereof known in the art as crude or polymeric MDI (polymethylene polyphenylene polyisocyanates) are especially useful.

Representative examples of suitable polyisocyanates include ethylene diisocyanate, 1,4-tetramethylene diisocyanate, 1,6-hexamethylene diisocyanate, trimethyl hexamethylene diisocyanate, 1,1,2-dodecane diisocyanate, cyclobutane-1,3-diisocyanate, cyclohexane-1,3-and 1,4-diisocyanate (and mixtures of these isomers), diisocyanto-3,3,5-trimethyl-5-isocyanatomethyl cyclohexane, 2,4- and 2,6-toluene diisocyanate (and mixtures of these isomers), diphenylmethane-2,4'- and/or 4,4'-diisocyanate, naphalene-1,5-diisocyanate, the reaction products of four equivalents of the above-mentioned isocyanate-containing compounds with compounds containing two isocyanate-reactive groups, triphenyl methane-4,4',4"-triisocyanate, polymethylene polyphenylene polyisocyanates, m- and p-isocyanatophenyl sulfonyl isocyanates, perchlorinated aryl polyisocyanates, polyisocyanates containing carbodiimide groups, norbornane diisocyanates, polyisocyanates containing allophanate groups, polyisocyanates containing polyisocyanurate groups, polyisocyanates containing urethane groups, polyisocyanates containing biuret groups, polyisocyanates produced by telomerization reactions, polyisocyanates containing ester groups, reaction products of the above-mentioned diisocyanates with acetals, polyisocyanates containing polymeric fatty acid esters, and mixtures thereof. Distillation residues (obtained in the commercial production of isocyanates) having isocyanate groups can also be used alone or in solution in one or more of the above-mentioned polyisocyanates.

Polyols suitable for use in the process of this invention are those having at least two isocyanate-reactive hydrogen atoms in the form of a hydroxyl group. Preferred polyols are those having from 2 to about 50, preferably from 2 to about 8, more preferably from 2 to about 4, hydroxyl groups. Such polyols can be, e.g., polyesters, polyethers, polythioethers, polyacetals, polycarbonates, polymethacrylates, polyester amides, or hydroxyl-containing prepolymers of these compounds and a less than stoichiometric amount of polyisocyanate. Generally, the polyol compounds utilized in the preferred process have a weight average molecular weight of from about 50 to about 50,000, preferably from about 500 to about 25,000.

Representative examples of suitable polyols have been described, e.g., by J. H. Saunders and K. C. Frisch in High Polymers, Volume XVI, "Polyurethanes," Part I, pages 32–54 and 65–88, Interscience, New York (1962). Mixtures of such compounds are also useful, and, in some cases, it is particularly advantageous to combine low-melting and high-melting compounds with one another, as described in DE 2,706,297 (Bayer AG). Useful polyols include ethylene glycol, 1,2- and 1,3-propylene glycol, 1,4- and 2,3-butylene glycol, 1,5-pentane diol, 1,5-hexane diol, 1,8-octane diol, neopentyl glycol, 1,4-bis (hydroxymethyl)cyclohexane, 2-methyl-1,3-propane diol, dibromobutene diol, glycerol, trimethylolpropane, 1,2,6-hexanetriol, trimethylolethane, pentaerythritol, mannitol, sorbitol, diethylene glycol, triethylene glycol, tetraethylene glycol, higher polyethylene glycols, dipropylene glycol, higher propylene glycols, dibutylene glycol, higher polybutylene glycols, 4,4'-dihydroxydiphenylpropane, and dihydroxymethyl hydroquinone.

In another aspect, the precursors of the foamable polymer of the present invention include a phenol and an aldehyde. In making the phenolic-based foam, the aldehyde, phenol and azeotrope-like composition can generally be combined, thoroughly mixed (using, e.g., any of the various known types of mixing head and spray apparatus), and permitted to expand and cure into a cellular polymer.

It is often convenient; but not necessary to preblend certain of the components of the foamable composition prior to reaction of the aldehyde and the phenol. For example, the azeotrope-like composition may be added to the phenol to form a first mixture and then blended with the aldehyde before vaporization and polymeric foam formation. Alternatively, the azeotrope-like composition can be added to the aldehyde to form a first mixture and then blended with the phenol before vaporization and polymeric foam formation. One can add hexafluoropropylene dimer to the aldehyde to form a pre-mixture, then add the hydrocarbon or hydrofluorocarbon and then bend the resultant mixture with the phenol. As well, one can add hexafluoropropylene dimer to the phenol to form a pre-mixture and then add the hydrocarbon or hydrofluorocarbon and then bend the resultant mixture with the aldehyde. In another aspect, hexafluoropropylene dimer is added to the phenol to form a first pre-mixture, the hydrocarbon or hydrofluorocarbon is added to the aldehyde to form a second pre-mixture and the first and second pre-mixtures are blended together. Also, hexafluoropropylene dimer can be added to the aldehyde to form a first pre-mixture, the hydrocarbon or hydrofluorocarbon is added to the phenol to form a second pre-mixture and the first and second pre-mixtures are blended together.

Catalysts suitable for use in the process for preparing polymeric foam of the invention include compounds that greatly accelerate the reaction of the polyol-containing compounds with the isocyanates (or polyisocyanates). When used, catalysts are generally present in amounts sufficient to be catalytically effective. Suitable catalysts include organic metal compounds (preferably, organic tin compounds), which can be used alone or, preferably, in combination with strongly basic amines. Representative examples of these and other types of suitable catalysts are described in U.S. Pat. No. 4,972,002 (Volkert), the descriptions of which are incorporated herein by reference.

The process of the invention may further comprise adding a surfactant to the foamable mixture comprising the azeotrope-like composition and at least one foamable polymer or the precursors of at least one foamable polymer. Suitable surfactants include fluorochemical surfactants, organosilicone surfactants, polyethylene glycol ethers of long chain alcohols, tertiary amine or alkanolamine salts of longchain alkyl acid sulfate esters, alkyl sulfonate esters, alkyl arylsulfonic acids, fatty acid alkoxylates, and mixtures thereof. Surfactant is generally employed in amounts sufficient to stabilize the foaming reaction mixture against collapse and the formation of large, uneven cells. Organosilicone surfactants and fluorochemical surfactants are preferred.

Foams prepared from the process of the invention can vary in texture from vary in texture from very soft types useful in upholstery applications to rigid foams useful as structural or insulating materials. The foams can be used, for example, in the automobile, shipbuilding, aircraft, furniture, and athletic equipment industries, and are especially useful as insulation materials in the construction and refrigeration industries.

The cleaning process of the present invention can be carried out by contacting a contaminated substrate with one of the azeotrope-like compositions of this invention until the contaminants on the substrate are dissolved, dispersed, or displaced in or by the azeotrope-like composition, and then removing (for example by rinsing the substrate with fresh, uncontaminated azeotrope-like composition or by removing a substrate immersed in an azeotrope-like composition from the bath and permitting the contaminated azeotrope-like composition to flow off of the substrate) the azeotrope-like composition containing the dissolved, dispersed, or displaced contaminant from the substrate. The azeotrope-like composition can be used in either the vapor or the liquid state (or both), and any of the known techniques for "contacting" a substrate can be utilized. For example, the liquid azeotrope-like composition can be sprayed or brushed onto the substrate, the vaporous azeotrope-like composition can be blown across the substrate, or the substrate can be immersed in either a vaporous or a liquid azeotrope-like composition. Elevated temperatures, ultrasonic energy, and/or agitation can be used to facilitate the cleaning. Various different solvent cleaning techniques are described by B. N. Ellis in *Cleaning and Contamination of Electronics Components and Assemblies*, Electrochemical Publications Limited, Ayr, Scotland, pages 182–94 (1986).

Both organic and inorganic substrates can be cleaned by the processes of the invention. Representative examples of the substrates include metals; ceramics; glass; silicon wafers; polymers such as: polycarbonate, polystyrene and acrylonitrile-butadiene-styrene copolymer; natural fibers (and fabrics derived therefrom) such as: cotton, silk, linen, wool, ramie; fur; leather and suede; synthetic fibers (and fabrics derived therefrom) such as: polyester, rayon, acrylics, nylon, polyolefin, acetates, triacetates and blends thereof; fabrics comprising a blend of natural and synthetic fibers; and composites of the foregoing materials. The process is especially useful in the precision cleaning of electronic components (e.g., circuit boards), optical or magnetic media, and medical devices and medical articles such as syringes, surgical equipment, implantable devices, and prosthesis.

The cleaning process of the invention can be used to dissolve or remove most contaminants from the surface of a substrate. For example, materials such as light hydrocarbon contaminants; higher molecular weight hydrocarbon contaminants such as mineral oils, greases, cutting and stamping oils and waxes, fluorocarbon contaminants such as perfluoropolyethers, bromotrifluoroethylene oligomers (gyroscope fluids), and chlorotrifluoroethylene oligomers (hydraulic fluids, lubricants); silicone oils and greases; solder fluxes; particulates; and other contaminants encountered in precision, electronic, metal, and medical device cleaning can be removed. The process is particularly useful for the removal of hydrocarbon contaminants (especially, light hydrocarbon oils), fluorocarbon contaminants and particulates.

The azeotrope-like compositions of the present invention are also useful for extraction. Here, cleaning involves removing contaminants (e.g., fats, waxes, oils, or other solvents) by dissolution or displacement of these materials from substances (e.g., naturally occurring materials, foods, cosmetics, pharmaceuticals).

The azeotrope-like compositions can also be used in coating deposition applications, where the azeotrope-like composition functions as a carrier for a coating material to enable deposition of the material on the surface of a substrate. The invention thus also provides a coating composition comprising the azeotrope-like composition and a process for depositing a coating on a substrate surface using the azeotrope-like composition. The process comprises the step of applying to at least a portion of at least one surface of a substrate a coating of a liquid coating composition comprising (a) an azeotrope-like composition; and (b) at least one coating material that is soluble or dispersible in the azeotrope-like composition. The coating composition can further comprise one or more additives (e.g., surfactants, coloring agents, stabilizers, anti-oxidants, flame retardants, and the like). Preferably, the process further comprises the step of removing the azeotrope-like composition from the deposited coating by, e.g., allowing evaporation (which can be aided by the application of, e.g., heat or vacuum).

The coating materials that can be deposited by the process include pigments, silicone lubricious additives, stabilizers, adhesives, anti-oxidants, dyes, polymers, pharmaceuticals, cosmetics, release agents, inorganic oxides, and the like, and combinations thereof. Preferred materials include perfluoropolyethers, hydrocarbons, and silicone lubricious additives; amorphous copolymers of tetrafluoroethylene; polytetrafluoroethylene; and combinations thereof. Representative examples of materials suitable for use in the process include titanium dioxide, iron oxides, magnesium oxide, perfluoropolyethers, polysiloxanes, stearic acid, acrylic adhesives, polytetrafluoroethylene, amorphous copolymers of tetrafluoroethylene, and combinations thereof. Any of the substrates described above (for cleaning applications) can be coated via the process of the invention. The process can be particularly useful for coating magnetic hard disks or electrical connectors with perfluoropolyether lubricants or medical devices with silicone lubricious additives.

To form a coating composition, the components of the composition (i.e., the azeotrope-like composition, the coating material(s), and any additive(s) utilized) can be combined by any conventional mixing technique used for dissolving, dispersing, or emulsifying coating materials, e.g., by mechanical agitation, ultrasonic agitation, manual agitation, and the like. The azeotrope-like composition and the coating material(s) can be combined in any ratio depending upon the desired thickness of the coating, but the coating material(s) preferably constitute from about 0.1 to about 10 weight percent of the coating composition for most coating applications.

The deposition process of the invention can be carried out by applying the coating composition to a substrate by any conventional technique. For example, the composition can be brushed or sprayed (e.g., as an aerosol) onto the substrate, or the substrate can be spin-coated. Preferably, the substrate is coated by immersion in the composition. Immersion can be carried out at any suitable temperature and can be maintained for any convenient length of time. If the substrate is a tubing, such as a catheter, and it is desired to ensure that the composition coats the lumen wall, it may be advantageous to draw the composition into the lumen by the application of reduced pressure.

After a coating is applied to a substrate, the azeotrope-like composition can be removed from the deposited coating by evaporation. If desired, the rate of evaporation can be accelerated by application of reduced pressure or mild heat. The coating can be of any convenient thickness, and, in practice, the thickness will be determined by such factors as the viscosity of the coating material, the temperature at which the coating is applied, and the rate of withdrawal (if immersion is utilized).

The azeotrope-like compositions can also be used as heat-transfer fluids in heat-transfer processes where the heat-transfer fluids can transfer thermal energy (i.e., heat) either in a direct or indirect manner. Direct heat transfer (sometimes called "direct contact heat transfer") refers to a heat-transfer process wherein a heat-transfer fluid conducts heat directly (i.e., through conduction and/or convection) to and/or from a heat sink or source to a fluid by directly contacting the fluid with the heat sink or source. Examples of direct heat transfer include the immersion cooling of electrical components and the cooling of an internal combustion engine.

Indirect heat transfer refers to a heat-transfer process wherein a heat-transfer fluid (sometimes called a "working fluid") conducts heat to and/or from a heat sink or source without directly contacting the fluid with the heat sink or source. Examples of indirect heat transfer include refrigeration, air conditioning and/or heating (e.g., using heat pumps) processes, such as are used in buildings, vehicles and stationary machinery. In one embodiment, the present invention provides a process for transferring heat comprising employing an azeotropic composition in this invention as a secondary loop refrigerant. In this embodiment, the secondary loop refrigerant (i.e., a wide temperature range liquid fluid) provides a means for transferring heat between the heat source (i.e., object to be cooled) and the primary loop refrigerant (i.e., a low temperature-boiling fluid which accepts heat by expanding to a gas and rejects heat by being condensed to a liquid, typically by using a compressor). Examples of equipment in which the azeotropic composition of this invention may be useful include, but are not limited to, centrifugal chillers, household refrigerator/freezers, automotive air conditioners, refrigerated transport vehicles, heat pumps, supermarket food coolers and display cases, and cold storage warehouses.

In indirect heat-transfer processes, lubricious additives for heat transfer can be incorporated in the working fluid where moving parts are involved to ensure that the moving parts (e.g., pumps and valves) continue to work over long periods of time. These lubricious additives should possess good thermal and hydrolytic stability and should exhibit at least partial solubility in the fluid. Examples of suitable lubricious additives include mineral oils, fatty esters, highly halogenated oils such as chlorotrifluoroethylene-containing polymers, and synthetic lubricious additives such as, alkylene oxide polymers.

The azeotrope-like compositions of the present invention can be used to formulate working fluids or lubricants that comprise the azeotrope-like compositions of the present invention and at least one fully volatile lubricious additive. A lubricious additive for working operations is defined herein as an additive that modifies the coefficient of friction between a workpiece and tooling. The azeotrope-like composition with the lubricious additive form the working fluid for the working operation. Working operations include metal, cermet, and composite workpieces.

Metals include: refractory metals such as tantalum, niobium, molybdenum, vanadium, tungsten, hafnium, rhenium, and titanium; precious metals such as silver, gold, and platinum; high temperature metals such as nickel, titanium alloys, and nickel chromes; and other metals including magnesium, copper, aluminum, steel (including stainless steels), and other alloys such as brass, and bronze. These working fluids lubricate machining surfaces, resulting in a smooth and substantially residue-free machined workpiece surface. The working fluids of the present invention in these operations also cool the machining environment (i.e., the surface interface between a workpiece and a machining tool) by removing heat and particulate matter therefrom.

Cermets are defined as a semisynthetic-product consisting of a mixture of ceramic and metallic components having physical properties not found solely in either one alone. Examples include, but are not limited to, metal carbides, oxides, and suicides. See Hawley's Condensed Chemical Dictionary, 12$^{th}$ Edition, Van Nostrand Reinhold Company, 1993.

Composites are described herein as laminates of high temperature fibers in a polymer matrix, for example, a glass or carbon fiber in an epoxy resin.

This working fluid is formulated so that the cutting and forming processes are lubricated to reduce friction, heat build-up in the tool or workpiece, and prevent material transfer from the workpiece to the tool. The working fluid fully wets the working tooling and the azeotrope-like composition evaporates from the working tool and workpiece such that the lubricious additive is present as a thin film that reduces friction and heat build-up on the surfaces of the tool and workpiece, and prevents material transfer from the workpiece to the tooling. The lubricious additive is selected such that it is sufficiently high in boiling point to lubricate the working process without evaporating prematurely and still low enough in boiling point to fully evaporate from the working process so that little or no residue remains. Examples of lubricious additives for working operations include, but are not limited to, esters of C 8 to C 14 fatty acids, alkylene glycol ethers, hydrocarbon distillates, and esters of lactic acid.

In each of the described uses, the azeotrope-like or azeotrope composition can be used per se, or a blend of azeotrope-like compositions may be used, provided the blend is azeotrope-like. Similarly, minor amounts of cosolvents can be added to the azeotrope-like compositions, provided the addition does not disrupt the azeotropic behavior, or that the addition produces a ternary azeotrope. Useful co-solvents may include CFCs, HCFCs, HFCs, hydrocarbons, hydrochlorocarbons (HCCs), or water. Representative examples of suitable co-solvents include 1,1-dichloro-1-fluoroethane, 1,1-dichloro-2,2,2-trifluoroethane, 1-hydropentadecafluoroheptane, 1,1,1,2-tetrafluoroethane, chlorodifluoromethane, 1,1,1,3,3-pentafluoropropane, trans-1,2-dichloroethene, 1-chloro-1,1-difluoroethane, and 2-chloropropane; chlorofluorocarbons, e.g., fluorotrichloromethane; water (which reacts with isocyanate to produce carbon dioxide); saturated perfluorochemicals, e.g., perfluoropentane, perfluorohexane, and perfluoro(N-methylmorpholine); and mixtures thereof.

This invention is further illustrated by the following examples, but the particular materials and amounts thereof recited in these examples, as well as other conditions and details, should not be construed to unduly limit this invention.

EXAMPLES

The preparation, identification and testing of the azeotrope-like compositions of this invention are further described in the following examples. The particular materials and amounts thereof recited in these examples, as well as other conditions and details, should not be construed to unduly limit this invention. Unless otherwise specified, all percentages, proportions and ratios are by weight.

Preparation of Hexafluoropropylene Dimer

Hexafluoropropylene dimer was prepared according to methods described in U.S. Pat. No. 5,254,774. The hexafluoropropylene dimer used in the following examples was 98% pure perfluoro-4-methyl-pent-2-ene (combined cis- and trans-isomers, approximately 5:95), according to NMR analysis.

Examples 1–4

Various mixtures of hexafluoropropylene dimer and hydrocarbon or hydrofluorocarbon were distilled at ambient (729 to 735 torr) pressure to identify whether they formed binary azeotropes, and if so, the composition (% by weight) and boiling point (b.p ° C.) of the azeotrope, using the following procedure. The mixtures were prepared and distilled at ambient lab pressure (729 to 735 torr) in a concentric tube distillation column (Model 933 available from Ace Glass, Vinland, N.J.). In each case, the distillation was allowed to equilibrate at total reflux for at least 60 minutes. For each distillation, six successive distillate samples, each approximately 5 percent by volume of the total liquid charge, were taken while operating the column at a liquid reflux ratio of 20 to 1. The compositions of the distillate samples were then analyzed using an HP-5890 Series II Plus Gas Chromatograph with an RTX-200 capillary column (available from Restek Corporation, Bellefonte, Pa.) and Nukol capillary column (available from Supelco, Bellefonte, Pa.) or a Quadrex 007 Series Methyl Silicone capillary column (available from Quadrex Corporation, New Haven, Conn.) and a thermal conductivity detector. The boiling point of each distillate was measured using a thermocouple. Following this test procedure, azeotropes of perfluoro-4-methyl-2-pentene were identified with cyclopentane, n-pentane, isopentane and 1,1,1,3,3-pentafluorobutane.

In TABLE 1 shown below, the compositions (% by weight) and boiling points (at noted pressure) of the four azeotropes are presented as Examples 1–4

TABLE 1

| Example | Composition | b.p. (° C.) | Pressure (torr) |
|---|---|---|---|
| 1 | 22.6% cyclopentane<br>77.4% hexafluoropropylene dimer | 32 | 729 |
| 2 | 32.5% n-pentane<br>67.5% hexafluoropropylene dimer | 27 | 731 |
| 3 | 41.4% isopentane<br>58.6% hexafluoropropylene dimer | 22 | 735 |
| 4 | 45.6% 1,1,1,3,3-pentafluorobutane<br>54.4% hexafluoropropylene dimer | 34 | 730 |

Examples 5–8

Percentage ranges for azeotrope-like compositions of the invention were identified by determining boiling points of test mixtures of hexafluoropropylene dimer with either cyclopentane, n-pentane, isopentane or 1,1,1,3,3-pentafluorobutane using an ebulliometer or boiling point apparatus (specifically a Model MBP-100 available from Cal-Glass for Research, Inc, Costa Mesa, Calif.). 25 to 30 mL of the lower boiling component of the test compositions was added to the boiling point apparatus. The liquid was heated and allowed to equilibrate to its boiling point (typically about 30 minutes). After equilibration, the boiling point was recorded, approximately 1.0 mL aliquot of the higher boiling component was added to the apparatus, and the resulting new composition was allowed to equilibrate for about 10 minutes, at which time the boiling point was recorded. The test continued basically as described above, with additions to the test mixture of about 1.0 mL of the higher boiling point component occurring every 10 minutes until 25 to 30 mL of the higher boiling point component had been added. The test was repeated by placing the higher boiling component into the apparatus and adding approximately 1.0 mL aliquots of the lower boiling component. The presence of an azeotrope-like composition was noted when the test mixture exhibited a lower boiling point than the boiling point of the lower boiling component.

The resulting azeotrope-like composition ranges are presented in TABLE 2. All boiling point determinations were run at standard pressure (760±1 torr).

TABLE 2

| Example | HC or HFC | HC or HFC Conc. (wt. % range) | hexafluoropropylene dimer Conc (wt. % range) |
|---|---|---|---|
| 5 | cyclopentane | 1–98.5 | 1.5–99 |
| 6 | n-pentane | 5–99 | 1–95 |
| 7 | isopentane | 10.5–99 | 1–89.5 |
| 8 | 1,1,1,3,3-pentafluorobutane | 10–99 | 1–90 |

We claim:
1. An azeotrope-like composition comprising:
(a) hexafluoropropylene dimer; and
(b) a hydrocarbon or a hydrofluorocarbon;
wherein said composition is selected from the group consisting of:
(i) compositions consisting essentially of about 2 to about 99 weight percent hexafluoropropylene dimer and about 1 to about 98 weight percent cyclopentane that boil below about 47° C. at about 760 torr;
(ii) compositions consisting essentially of about 1 to about 90 weight percent hexafluoropropylene dimer and about 10 to about 99 weight percent isopentane that boil below about 27.5° C. at about 760 torr; and
(iii) compositions consisting essentially of about 1 to about 90 weight percent hexafluoropropylene dimer and about 10 to about 99 weight percent 1,1,1,3,3-pentafluorobutane that boil below about 40° C. at about 760 torr.

2. An azeotrope-like composition according to claim 1 comprising:
(a) hexafluoropropylene dimer; and
(b) a hydrocarbon or a hydrofluorocarbon;
wherein said composition is selected from the group consisting of:
(i) compositions consisting essentially of about 5 to about 98 weight percent hexafluoropropylene dimer and about 2 to about 95 weight percent cyclopentane that boil below about 44° C. at about 760 torr;
(ii) compositions consisting essentially of about 5 to about 88 weight percent hexafluoropropylene dimer and about 12 to about 95 weight percent isopentane that boil below about 27° C. at about 760 torr; and
(iii) compositions consisting essentially of about 5 to about 87 weight percent hexafluoropropylene dimer and about 95 to about 13 weight percent 1,1,1,3,3-pentafluorobutane that boil below about 39° C. at about 760 torr.

3. An azeotrope-like composition according to claim 1 consisting essentially of:
(a) hexafluoropropylene dimer; and
(b) a hydrocarbon or a hydrofluorocarbon;
wherein said composition is selected from the group consisting of:
(i) compositions consisting essentially of about 12 to about 96 weight percent hexafluoropropylene dimer and about 4 to about 88 weight percent cyclopentane that boil below about 40° C. at about 760 torr;
(ii) compositions consisting essentially of about 11 to about 85 weight percent hexafluoropropylene dimer and about 15 to about 89 weight percent isopentane that boil below about 26° C. at about 760 torr; and (iii) compositions consisting essentially of about 10 to about 84 weight percent hexafluoropropylene dimer and about 16 to about 90 weight percent 1,1,1,3,3-pentafluorobutane that boil below about 38° C. at about 760 torr.

4. An azeotrope composition consisting essentially of:
(a) hexafluoropropylene dimer; and
(b) a hydrocarbon or a hydrofluorocarbon;
wherein said composition is selected from the group consisting of:
  (i) compositions consisting essentially of about 77.4 weight percent hexafluoropropylene dimer and about 22.6 weight percent cyclopentane that boil at about 32° C. at about 729 torr;
  (ii) compositions consisting essentially of about 67.5 weight percent hexafluoropropylene dimer and about 32.5 weight percent n-pentane that boil at about 27° C. at about 731 torr;
  (iii) compositions consisting essentially of about 58.6 weight percent hexafluoropropylene dimer and about 41.4 weight percent isopentane that boil at about 22° C. at about 735 torr; and
  (iv) compositions consisting essentially of about 54.4 weight percent hexafluoropropylene dimer and about 45.6 weight percent 1,1,1,3,3-pentafluorobutane that boil at about 34° C. at about 730 torr.

* * * * *

UNITED STATES PATENT AND TRADEMARK OFFICE
CERTIFICATE OF CORRECTION

PATENT NO. : 7,022,658 B2 Page 1 of 1
APPLICATION NO. : 10/673821
DATED : April 4, 2006
INVENTOR(S) : David A. Hesselroth It is certified that error appears in the above-identified patent and that said Letters Patent is hereby corrected as shown below:

Col. 1
Line 44, delete "con positions" and insert -- compositions --, therefor.

Col. 9
Line 40, delete "waxes," and insert -- waxes; --, therefor.

Col. 11
Line 65, delete "suicides." and insert -- silicides. --, therefor.

Signed and Sealed this

Eighteenth Day of March, 2008

JON W. DUDAS
*Director of the United States Patent and Trademark Office*